United States Patent [19]

König et al.

[11] 4,003,884

[45] Jan. 18, 1977

[54] PEPTIDES HAVING LH-RH/FSH-RH ACTIVITY

[75] Inventors: Wolfgang König, Hofheim, Taunus; Rolf Geiger; Jürgen K. Sandow, both of Frankfurt am Main, all of Germany

[73] Assignee: Hoechst Aktiengesellschaft, Frankfurt am Main, Germany

[22] Filed: May 16, 1975

[21] Appl. No.: 578,196

[30] Foreign Application Priority Data

May 18, 1974 Germany .......................... 2424287
Dec. 20, 1974 Germany .......................... 2460333
Dec. 20, 1974 Germany .......................... 2460335

[52] U.S. Cl. ..................... 260/112.5 LH; 424/177
[51] Int. Cl.² ................ C07C 103/52; A61K 37/00
[58] Field of Search .......................... 260/112.5 LH

[56] References Cited

UNITED STATES PATENTS

| | | | |
|---|---|---|---|
| 3,780,014 | 12/1973 | Flouret | 260/112.5 LH |
| 3,790,554 | 2/1974 | Flouret | 260/112.5 LH |
| 3,803,117 | 4/1974 | Flouret | 260/112.5 LH |
| 3,826,796 | 7/1974 | Sarantakis et al. | 260/112.5 LH |
| 3,835,108 | 9/1974 | Immer et al. | 260/112.5 LH |
| 3,856,769 | 12/1974 | Sakakibara et al. | 260/112.5 LH |
| 3,880,825 | 4/1975 | Sakakibara et al. | 260/112.5 LH |
| 3,888,838 | 10/1975 | Immer et al. | 260/112.5 LH |
| 3,892,723 | 7/1975 | McKinley et al. | 260/112.5 LH |
| 3,901,872 | 8/1975 | McKinley et al. | 260/112.5 LH |
| 3,914,412 | 10/1975 | Gendrich et al. | 260/112.5 LH |

*Primary Examiner*—Lewis Gotts
*Assistant Examiner*—Reginald J. Suyat
*Attorney, Agent, or Firm*—Curtis, Morris & Safford

[57] ABSTRACT

Peptides having LH-RH/FSH-RH activity useful for treatment of male and female sterility.

7 Claims, No Drawings

PEPTIDES HAVING LH-RH/FSH-RH ACTIVITY

The luteotrophic hormone (LH) and the follicle stimulating hormone (FSH) releasing hormone LH-RH/FSH-RD having the structure

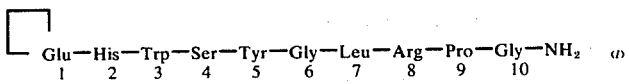

(Biochem. Biophys. Res. Commun. 43, 1334 (1971) has already been modified in many positions. In this context it has been found that by substituting Gly in the position 6 by D-alanine (Biochemistry 12, 4616 (1973)) or by substituting Gly-$NH_2$ in the position 10 by ethyl amide, propyl amide or isopropyl amide (J. Med. Chem. 16, 1144 (1973)) the activity is increased.

By replacing arginine by lysine or ornithine (J. Med. Chem. 15, 623 (1972)), tyrosine by phenylanaline (J. Med. Chem. 16, 827 (1973)), serine by alanine, (Biochem. Biophys. Res. Commun. 49, 1467 (1972) or threonine (J. Med. Chem. 16, 1140 – 43 (1973)), the activity has not been increased but maintained to a percentage of about 10 to 50%.

By changing the position 7 only derivatives having a lower activity have been hitherto obtained, whereby starting from isoleucine via norleucine, valine, alanine and glycine the activity has decreased from 45% to 3%. (Biochem. Biophys. Res. Commun. 49, 698 (1972)).

The invention relates to peptides of the general formula

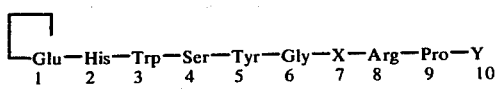

wherein X represents Ser (Bu$^t$), Cys (Bu$^t$), Asp (OBu$^t$), Glu (OBu$^t$), Orn(Boc) or Lys(Boc) and Y represents glycinamide or a NH-alkyl group, wherein the alkyl radical contains 1 to 3 carbon atoms and may be substituted by OH group or halogen atoms, or the NH-cyclopropyl radical and, if desired, Trp may be substituted by pentamethylphenylalanine, Ser by Ala or Thr, Tyr by Phe, Gly by D-amino acids, which correspond to the naturally occuring L-amino acids, Arg may be substituted by Orn, Lys or Homoarginine.

The invention further relates to a process for preparing these peptides, which comprises preparing the peptides either a. by fragment condensation usual in peptide chemistry of peptide fragments according to the condensation scheme 1 − 6 + 7 − 10, 1−3 + 4 − 10 or 1 − 2 + 3 − 10 or b. by stepwise synthesis, whereby other functional groups are blocked intermediately by protective groups capable of being split off by hydrogenation, or capable of being split off in an alkaline or slightly acidic medium.

Considering that a change in position 7 only brings about derivatives having a weaker activity, the result is surprising according to which the activity is increased when replacing leucine by the amino acid radicals indicated for X and moreover, a clear depot effect is observed. Especially active LH—RH — analogues are obtained if in the compounds of the invention in position 6 an additional exchange in the indicated sense takes place and/or Y in the general formula represents an optionally substituted NH-alkyl group.

As D-amino acids instead of Gly in position 6 there are preferably considered: D-alanine, D-leucine, D-phenylalanine or D-tryptophane.

As compounds of the invention the following LH—RH analogous compounds are especially considered:

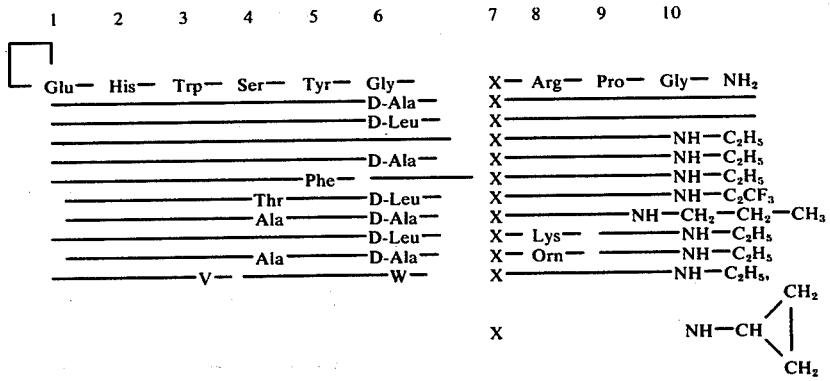

where X has the meaning indicated above, V stands for L-pentamethyl-phenyl-alanine and W for α.α-dimethylglycine.

In the synthesis of the compounds of the invention there are used the condensation methods according to which the tert.-butyl radicals which can be easily split off in an acidic medium, are not split off.

In fragment coupling according to (a), a. there are preferably used the azide coupling proceeding without racemization or the DCC 1-hydroxybenzotriazol- or DCC 3-hydroxy-4-oxo-3,4-dihydro-1,2,3-benzotriazine method. There may also be used activated esters of fragments.

For the stepwise condensation of amino acids according to b. there are especially suitable activated esters of benzyloxycarbonylamino acids, as for example N- hydroxy-succinimide esters or 2,4,5-trichloro-phenyl esters and 4-nitrophenyl esters. The aminolysis of the two latter active esters may be catalysed very well by N-hydroxy compounds, which approximately have the acidity of the acetic acid.

As intermediate amino protective groups there may be used groups capable of being split off by hydrogenation, as for example the benzyloxycarbonyl radical or groups capable of being split off in a slightly acidic medium, as for example the 2-(p-diphenyl)-isopropyloxy-carbonyl- or 2-(3,5-dimethoxyphenyl)-isopropyloxycarbonyl radical.

In the case of the S-tert.-butyl group very stable in the acidic medium there may also be used the Boc or Z-protective groups capable of being split off in an acidic medium. In this case the Boc radical may be split off with trifluoro-acetic acid or HCl/glacial acetic acid at room temperature. The radical Z may be acidically split off with HBr/glacial acetic acid or removed by catalytical hydrogenation. However, in the catalytical hydrogenation the addition of bases, as for example triethyl amine, N-ethyl morpholine or cyclohexyl amine is recommended in the presence of Cys ($Bu^t$). Furthermore, in the presence of Cys ($Bu^t$), the hydroxy functions of serine or tyrosine, additionally to the protective groups capable of being split off in an alkaline medium and by hydrogenation, may also be protected intermediately by the tert.-butyl group capable of being split off in an acidic medium.

The guanido function of the arginine may remain unprotected or may be blocked by a nitro group which is split off in the following hydrogenation. The OH-groups of the serine and tyrosine may be protected by groups of the benzyl type capable of being split off by hydrogenation. The phenolic OH-group of the tyrosine may be further protected by the ethoxycarbonyl radical capable of being split off in an alkaline medium. All protective groups mentioned may be split off selectively to the groups containing tert.-butyl in position 7.

The following reaction schemes may be used for example according to (a):

Reaction scheme 1:

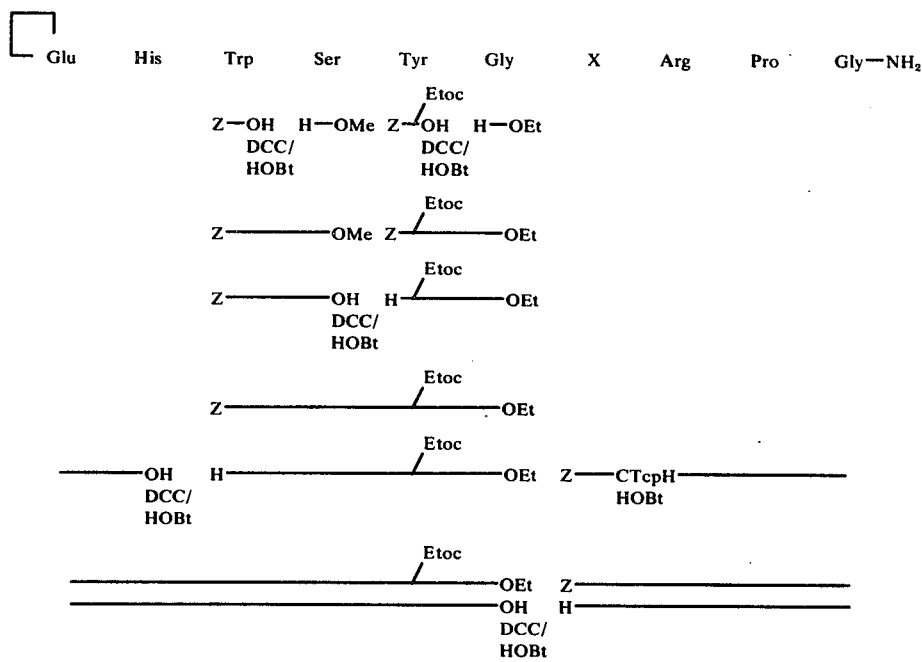

Reaction scheme 2:

-continued

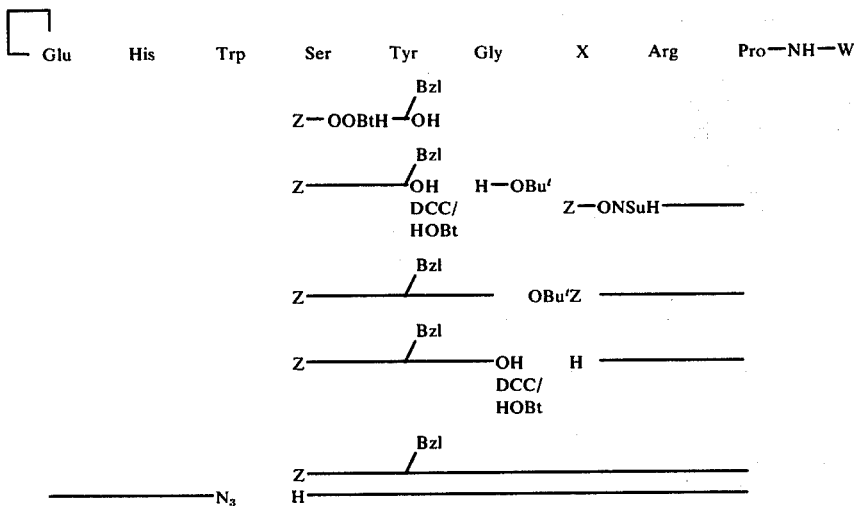

Reaction scheme 3:

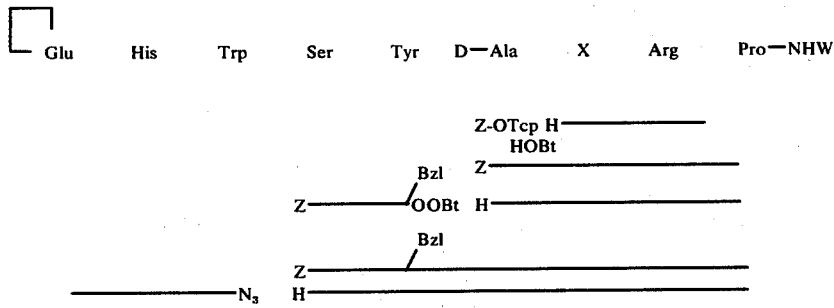

The abbreviations correspond to the proposals of the Iupac-Iub Commission, J.Biol. Chem. 247, 977 – 983 (1972).

Further abbreviations:
DCC = Dicyclohexyl carbodiimide
DCHA = Dicyclohexylamine
HOBt = 1-hydroxybenzotriazole
OOBt = 3-hydroxy-4-oxo-3,4-dihydro-1,2,3-benzotriazine ester
OTcp = 2,4,5-trichlorophenyl ester With regard to the 7-leucine-LH-RH-compounds in the ovulation test the compounds of the invention show an activity having more than the double effect. They represent novel medicaments which cause in case of insufficiency of hypothalamus and hypophysis the release of the luteinizing and the follicle stimulating hormone from the anterior lobe of the hypophysis and are, therefore, used for the treatment of female and male sterility in human beings and animals, as far as this sterility has a hypothalamic - hypophyseal origin. They may also be used as diagnostic agents for testing the function of the hypophysis.

Dissolved in a physiological sodium chloride solution, the compounds of the invention may be applied intravenously, intramuscularly or subcutaneously, they may be applied intranasally in the form of nose drops or nose spray. As therapeutic agents there are administered parenterally three daily dosage units of 0.03 – 0.5 mg in each case, as diagnostic agents parenterally 0.01 – 0.1 mg.

EXAMPLE 1: (in analogy to the reaction scheme 1)
⌐Glu-His-Trp-Ser-Tyr-Gly-Lys(Boc)-Arg-Pro-Gly-NH₂ a. H-Lys(Boc)-Arg-Pro-Gly-NH₂ . 2HCl 1.3 ml of N-ethylmorpholine and 5.6 g of Z-Lys(-Boc)-OTcp were added to a solution of 6.7 g (10 mmols) of H-Arg-Pro-Gly-NH₂ ditosylate and 1.35 g (10 mmols) of HOBt in 30 ml of dimethylformamide. The mixture was stirred for 5 hours at room temperature, the solution was evaporated and the residue was distributed between ethyl acetate and a 2N sodium hydroxide solution. The ethyl acetate phase was separated, dried with sodium sulfate and concentrated. The residue was triturated with ether. Yield: 7.5 g of amorphous substance. The substance was dissolved in 100 ml of methanol. A spatula tip of Pd/BaSo₄ catalyst was added, and the whole was hydrogenated while passing, while stirring, hydrogen through the solution. The pH-value of the solution was maintained at 4.5 with the aid of an autotitrator by addition of a 1N methanolic hydrochloric acid. When hydrogenation was finished the catalyst was suction-filtered and the filtrate concentrated. The residue was triturated with ether and suction-filtered. Yield: 5.45 g of amorphous substance. Since the substance was not homogeneous with regard to thin layer chromatography, the following purification of the column was carried out:

Composition of the column: 400 ml of glacial acetic acid, 800 ml of n-butanol and 4 liters of water were shaken. 300 ml of the upper phase were stirred with 240 g of Sephadex LH 20[(R)]. The total amount of the solvent was absorbed. The contents of the column thus pre-treated was suspended in a corresponding amount of the lower phase. The whole was allowed to swell and the column (1 m × 4 cm) was filled. The lower phase was eluted. On the column described above the substance was chromatographed in two phases with 2.7 g portions in each case. Yield of chromatographically pure substance: 3.5 g of amorphous substance (61%, calculated on H-Arg-Pro-Gly-$NH_2$-ditosylate).

$[\alpha]_D^{20} = -21.3°$ (c=1, in methanol b. Z-Trp-Ser-OMe 6.4 ml of N-ethylmorpholine and at 0° C, a solution of 10.5 g of DCC in 50 ml of tetrahydrofurane were added to a solution of 16.9 g (50 mmols) of Z-Trp-OH, 7.7 g (50 mmols) of H-Ser-OMe . HCl and 6.65 g (50 mmols) of HOBt in 100 ml of absolute tetrahydrofurane. The mixture was stirred for one hour at 0° C and for 2 hours at room temperature, the deposit was suction-filtered and the filtrate was concentrated. The residue was dissolved in ethyl acetate and successively extracted with saturated $NaHCO_3$-solution, $KHSO_4$-solution, saturated $NaHCO_3$-solution and water. The ethyl acetate phase was dried over $Na_2SO_4$ and concentrated. The remaining oil was dissolved in 120 ml of isopropanol. When standing in the refrigerator the substance was crystallized. Yield: 15.6 g (71%), melting point: 143° – 145° C. $[\alpha]_D^{25} = -16.8°$ (c=1, dimethylacetamide)

c. Z-Trp-Ser-OH 4.4 g (10 mmols) of Z-Trp-Ser-OMe were dissolved in 30 ml of dioxane/water (4:1) and mixed with a spatula tip of thymolphthaleine. The mixture was titrated, while stirring, with 1N NaOH until a constant blue color was obtained. 10 ml were consumed. 10 ml of 1N hydrochloric acid were added and the reaction mixture was evaporated. The residue was distributed between ethyl acetate and water. The ethyl acetate phase was dried with $Na_2SO_4$ and concentrated. The residue was triturated with petroleum ether. Yield: 3.2 g (75%). It was recrystallized from ethyl acetate/petroleum ether. Yield: 3 g (70%), melting point: 148° C.

$[\alpha]_D^{20} = -11.1°$ (c=1, dimethylacetamide).

d. Z-Tyr(Etoc)-Gly-OEt 12.8 ml of N-ethylmorpholine and 21 g of DCC, dissolved in 50 ml of dimethylformamide were added to a solution of 38.74 g (0.1 ml) of Z-Tyr(Etoc)-OH, 13.5 g (0.1 mol) of HOBt and 14 g (0.1 mol) of H-Gly-OEt.HCl in 250 ml of tetrahydrofurane and 50 ml of dimethylformamide. The whole was stirred for one hour at 0° C and for three hours at room temperature, the deposit was suction-filtered and the filtrate was concentrated. The resulting oil was dissolved in ethyl acetate and the solution was extracted successively with saturated $NaHCO_3$-solution, $KHSO_4$-solution, saturated $NaHCO_3$-solution and water. The ethyl acetate phase was dried over $Na_2SO_4$ and somewhat evaporated. A crystalline substance was precipitated from ethyl acetate with petroleum ether. Yield: 41.47 g (88%), melting point: 153°.

$[\alpha]_D^{25} = -16.2°$ (c=1, dimethylacetamide).

e. Z-Trp-Ser-Tyr(Etoc)-Gly-OEt 7.57 g (16 mmols) of Z-Tyr(Etoc)-Gly-OEt were dissolved in 200 ml of methanol and 40 ml of dimethylacetamide and hydrogenated catalytically as in test 1a. Yield: 4.75 g (79%). The 4.75 g (12.7 mmols) of H-Tyr(Etoc)-Gly-OEt.HCl obtained above were dissolved together with 5.39 g (12.7 mmols) of Z-Trp-Ser-OH and 1.7 g of HOBt in 40 ml of dimethylformamide. At 0° C, 1.63 ml of N-ethylmorpholine and 2.67 g of DCC dissolved in a small amount of dimethylformamide were added to this solution, while stirring. The mixture was allowed to stand for 85 hours at 2° C, the deposit was suction-filtered and the filtrate was concentrated. It was worked up as in test 1d). The residue was triturated with ether. Yield: 7.23 g (76%), melting point: 155° C.

$[\alpha]_D^{25} = -9.7°$ (c=1, dimethylacetamide).

f. ⌐Glu-His-Trp-Ser-Tyr-Gly-OH 5.24 g (7.03 mmols) of Z-Trp-Ser-Tyr(Etoc)-Gly.OEt were hydrogenated catalytically in methanol as in test 1a). Yield: 4.4 g (97%).

The 4.4 g (6.8 mmols) of H-Trp-Ser-Tyr(Etoc)-Gly-OEt.HCl were dissolved together with 2.25 g (7.44 mmols) of ⌐Glu-His-OH.2$H_2O$ and 1.83 g (13.5 mols) of HOBt in 20 ml of dimethylformamide. At 0° C, 0.88 ml (6.8 mmols) of N-ethylmorpholine and a solution of 1.5 g of DCC in a small amount of dimethylformamide were added to this solution. The mixture was stirred for one hour at 0° C and over night at room temperature. The deposit was suction-filtered and the filtrate was concentrated. The residue was triturated with ether. The ether was decanted. The whole was dissolved with a mixture of methanol/water (1:1) and chromatographed at the strongly basic ion exchanger Serdolit Blau[(R)]. The eluate was concentrated and the residue was dissolved in methanol. The methanolic solution was introduced dropwise into ether, while stirring. The precipitating amorphous material was suction-filtered. Yield: 3.4 g. The 3.4 g of ⌐Glu-His-Trp-Ser-Tyr(Etoc)-Gly-OEt were dissolved in methanol/water (1:1) and mixed with 6.5 ml of 1N NaOH. After 30 minutes at room temperature the mixture was neutralized with 1N HCl and concentrated. The residue was dissolved in water and chromatographed over Dowex 50 (200 – 400 mesh). It was eluted first with water and then until exhaustion with a 0.1 molar acetic acid. Then it was eluted with a 0.1 molar aqueous pyridine solution. The fractions containing the hexapeptide desired, were concentrated and reprecipitated from methanol/ether. Yield: 500 mg ($\triangleq$ 0.66 mmols $\triangleq$ ca. 10% calculated on H-Trp-Ser-Tyr(Etoc)-Gly-OEt), $[\alpha]_D^{20} = -7.9°$ (c=1, glacial acetic acid).

g. ⌐Glu-His-Trp-Ser-Tyr-Gly-Lys(Boc)-Arg-Pro-Gly-$NH_2$ 0.065 ml of N-ethylmorpholine and at 0° C, 110 mg of DCC were added to a solution of 380 mg of Glu-His-Trp-Ser-Tyr-Gly-OH (0.5 mmol), 314 mg (0.5 mmol) of H-Lys(Boc)-Arg-Pro-Gly-$NH_2$ . 2HCl and 135 mg (1 mmol) of HOBt in 5 ml of dimethylacetamide. The mixture was subsequently stirred for one hour at 0° C and allowed to stand for 28 hours at room temperature. Then 110 mg of DCC were added again, the whole was allowed to stand for 24 hours, the deposit was suction-filtered, the filtrate was concentrated and the residue triturated with ether. The solid product was suction-filtered (880 mg). For purification the crude substance was chromatographed in analogy to Example 1(a). 151 mg of a chromatographically pure substance were obtained (23%). Amino acid analysis: Ser (0.72), Glu (1.02), Pro (0.98), Gly (2.00), Tyr (0.97), Lys (1.00), His (0.91), Arg (1.03).

EXAMPLE 2: (in analogy to the reaction scheme 3)

⌐Glu-His-Trp-Ser-Tyr-D-Ala-Lys(Boc)-Arg-Pro-NH-$C_2H_5$ a. Z-Arg($Z_2$)-Pro-NH-$C_2H_5$

At 0° C, 6.5 ml of N-ethylmorpholine and 11 g of DCC were added to a solution of 8.9 g (50 mmols) of H-Pro-NH-$C_2H_5$ . HCl, 28.9 g (50 mmols) of Z-Arg($Z_2$)-OH and 6.75 g (50 mmols) of HOBt in 150 ml of methylene chloride, the whole was stirred for one hour at 0° C and allowed to stand over night at room temperature. The deposit was suction-filtered and the filtrate was concentrated. The residue was distributed between ethyl acetate and water. The ethyl acetate phase was extracted succesively with saturated NaHCO$_3$-solution, 2N H$_2$SO$_4$, saturated NaHCO$_3$-solution and with water, dried over Na$_2$SO$_4$ and concentrated. The residue was dissolved in isopropanol. An oil was precipitated with petroleum ether, which crystallized over night. Yield: 27.8 g (80%), melting point: 82° – 85° C $[\alpha]_D^{22} = -30.0°$ (c=1, methanol).

b. H-Arg-Pro-NH—$C_2H_5$ . 2 HCl 39.7 g (56.7 mmols) of Z-Arg($Z_2$)-Pro-NH-$C_2H_5$ were hydrogenated catalytically in methanol in analogy to Example 1(a).

Yield: 17.9 g (85%) $[\alpha]_D^{20} = -26.0°$ (c=1, methanol).

c. H-Lys(Boc)-Arg-Pro-NH-$C_2H_5$ . 2 HCl 0.65 ml of N-ethylmorpholine and 2.8 g (5 mmols) of Z-Lys(Boc)-OTcp were added to a solution of 1.85 g (5 mmols) of H-Arg-Pro-NH-$C_2H_5$ . 2 HCl, 675 mg (5 mmols) of HOBt in 10 ml of dimethylformamide. The whole was allowed to stir for 5 hours at room temperature, concentrated and the residue was distributed between ethyl acetate and saturated NaHCO$_3$-solution. The ethyl acetate solution was extracted again with a NaHCO$_3$ solution, dried with Na$_2$SO$_4$ and concentrated. It was triturated with diisopropyl ether and dried at the high vacuum. Yield: 3.4 g of amorphous substance. This substance was hydrogenated catalytically in methanol in analogy to Example 1(a). Yield: 2.4 g of amorphous substance (80%). Not homogenous with regard to thin layer chromatography (contaminated by three by-products).

d. H-D-Ala-Lys(Boc)-Arg-Pro-NH-$C_2H_5$ . 2 HCl

To a solution of 2.4 g (4 mmols) of H-Lys(Boc)-Arg-Pro-NH—$C_2H_5$ . 2 HCl and 540 mg (4 mmols) of HOBt in 15 ml of dimethylformamide 0.52 ml of N-ethylmorpholine and 1.6 g of Z-D-Ala-OTcp were added. The mixture was stirred for one hour at room temperature and concentrated. The residue was distributed between saturated NaHCO$_3$-solution and ethyl acetate. The ethyl acetate phase was extracted again with saturated Na HCO$_3$-solution, dried with Na$_2$SO$_4$ and evaporated. The residue was triturated with ether. Yield: 2.8 g of amorphous substance which was hydrogenated catalytically in methanol in analogy to Example 1(a). Since the substance was strongly contaminated it was purified in analogy to Example 1(a) by column chromatography. Yield of amorphous substance homogeneous with regard to thin layer chromatography: 1.22 g (45% calculated on the H-Lys(Boc)-Arg-Pro-NH-$C_2H_5$ . 2 HCl).

e. Z-Ser-Tyr(Bzl)-OH 7.68 g of Z-Ser-OOBt were added to a suspension of 5.52 g (20 mmols) of H-Tyr(Bzl)-OH in 60 ml of dimethylacetamide, and the mixture was stirred for 6 hours at room temperature. The undissolved material was suction-filtered and the filtrate cooled to 0° C was mixed with 300 ml of water. The deposit was suction-filtered, washed with a dimethylacetamide/water mixture (1:10) and water and stirred with 1N H$_2$SO$_4$. It was suction-filtered again and washed with water and dried. The ethyl acetate/petroleum ether was recrystallized. Yield: 7.35 g (75%), melting point: 166°, $[\alpha]_D^{20} = +20.9°$ (c = 1, methanol).

f. Z-Ser-Tyr(Bzl)-OOBt

At 0° C, 2.1 g of DCC were added to a solution of 4.92 g (10 mmols) of Z-Ser-Tyr(Bzl)-OH and 1.63 g (10 mmols) of HOOBt in 50 ml of absolute tetrahydrofurane, the whole was stirred for one hour at room temperature, 20 ml of dimethylformamide were added, the deposit was precipitated, and the whole was washed again with dimethylformamide. The filtrate was concentrated and the residue triturated with isopropanol and suction-filtered. It was washed with isopropanol and petroleum ether.

Yield: 4.5 g (71%), melting point: 175° – 177°.

g. H-Ser-Tyr-D-Ala-Lys(Boc)-Arg-Pro-NH-$C_2H_5$ . 2 HCl 0.237 ml of N-ethylmorpholine and 1.15 g (1.82 mmols) of Z-Ser-Tyr(Bzl)-OOBt were added to a solution of 1.22 g (1.82 mmols) of H-D-Ala-Lys(Boc)-Arg-Pro-NH-$C_2H_5$ . 2 HCl in 20 ml of dimethylformamide. The whole was allowed to stand over night at 4° C, and the next day a substance was precipitated with water and a 2N sodium hydroxide solution which was suction-filtered and dried. Yield: 1.4 g. In analogy to Example 1 this substance was hydrogenated catalytically in methanol. Yield: 1.28 g of amorphous substance (76% calculated on Z-Ser-Tyr(Bzl)-OOBt). The substance has not homogeneous with regard to thin layer chromatography (contaminated by three by-products).

h. ⎡Glu-His-Trp-Ser-Tyr-D-Ala-Lys(Boc)-Arg-Pro-NH-N$_2$H$_5$ . 2 HCl

To a solution of 695 mg (about 1.39 mmols) of Glu-His-Trp-NH-NH$_2$ in 10 ml of dimethylformamide 1 ml of 5.5N HCl/dioxane and 0.17 ml of tert.-butyl nitrite were added at 30° C. The temperature was raised to − 15° C and the mixture was stirred for 45 minutes at this temperature. Then it was cooled to −40° C, 1.28 g (1.39 mmols) of H-Ser-Tyr-D-Ala-Lys(Boc)-Arg-Pro-NH—$C_2$ H$_5$ . 2 HCl and 1.07 ml of ethylmorpholine were added, and the whole was allowed to stand over night at 0° C. The next day it was concentrated and the residue was triturated with ether. The crude product was purified chromatographically three times in analogy to Example 1(a).

Yield: 100 mg of chromatographically homogeneous product, $[\alpha]_D^{20} = -32.2°$ (c=1, water).

According to the amino acid analysis the product had a peptide content of 60%. Amino acid analysis: Ser(0.65), Glu (1.1), Pro (1.07), D-Ala (1.1), Tyr (0.88), Lys (1.00), His (1.1), Arg (0.78).

EXAMPLE 3 (in analogy to the reaction scheme 2, slightly varied)

⎡Glu-His-Trp-Ser-Tyr-Gly-Lys(Boc)-Arg-Pro-NH-$C_2H_5$ . 2 HCl a. Z-Ser-Tyr(Bzl)-Gly-OBu$^t$

To a solution of 24.7 g (50 mmols) of Z-Ser-Tyr(Bzl)-OH, 6.75 g (50 mmols) of HOBt and 8.4 g (50 mmols) of H-Gly-OBu$^t$ . HCl in 100 ml of dimethylformamide 6.5 ml of N-ethylmorpholine and at 0° C, 11 g of DCC were added, dissolved in a small amount of dimethylformamide. The mixture was stirred for one hour at 0° C and allowed to stand over night at room temperature. The deposit was suction-filtered and the filtrate concentrated. The residue was distributed between water and ethyl acetate. The ethyl acetate phase was extracted with a KHSO$_4$-solution, saturated NaHCO$_3$-solution and water, dried with Na$_2$SO$_4$ and concentrated. The ethyl acetate/petroleum ether was reprecipitated.

Yield: 26.8 g (88%), melting point: 123° – 125° C.

b. Z-Ser-Tyr(Bzl)-Gly-OH 20 g (33 mmols) of Z-Ser-Tyr(Bzl)-Gly-OBu$^t$ were dissolved in 100 ml of a 90% aqueous trifluoro-acetic acid. The mixture was allowed to stand at room temperature and was concentrated. The residue was triturated with ether, suction-filtered and dried. The ethyl acetate was recrystallized.

Yield: 10.1 g (56%), melting point: 197° – 198° C, $[\alpha]_D^{22} = -18.1°$ (c=1, methanol).

c. Z-Ser-Tyr(Bzl)-Gly-OTcp

To a solution of 5.49 g (10 mmols) of Z-Ser-Tyr(Bzl)-Gly-OH and 1.97 g of 2,4,5-trichlorophenol in 40 ml of tetrahydrofurane and 15 ml of dimethylformamide 2.2 g of DCC were added at 0° C. It was stirred for two hours at 0° C and for three hours at room temperature. The deposit was suction-filtered and the filtrate was concentrated. The residue was triturated with petroleum ether and suction-filtered. It was boiled with isopropanol, cooled and suction-filtered.

Yield: 6.3 g (86%), melting point: 152° – 160° C, $[\alpha]_D^{22} = -2.9°$ C (c=1, in dimethylformamide).

d. H-Ser-Tyr-Gly-Lys(Boc)-Arg-Pro-NH-$C_2H_5$ . 2 HCl

To a suspension of 2.4 g (4 mmols) of H-Lys(Boc)-Arg-Pro-NH—$C_2H_5$ . 2 HCl and 540 mg of HOBt in 30 ml of dimethylformamide 0.52 ml of N-ethylmorpholine and 2.92 g (4 mmols) of Z-Ser-Tyr(Bzl)-Gly-OTcp were added. The mixture was stirred over night at room temperature, concentrated, the residue was triturated twice with a 2N sodium hydroxide solution and once with water, distilled again with absolute alcohol and the residue was triturated with diisopropyl ether. Finally it was dried in high vacuum. 3.5 g of an amorphous substance were obtained, which were hydrogenated catalytically in methanol in analogy to Example 1(a). Yield: 3.4 g. The crude substance was purified in analogy to Example 1(a) by column chromatography.

Yield of amorphous substance homogeneous with regard to thin layer chromatography: 1 g, $[\alpha]_D^{20} = -36.0°$, (c=1, methanol).

e. ⌐Glu-His-Trp-Ser-Tyr-Gly-Lys(Boc)-Arg-Pro-NH-$C_2H_5$ . 2 HCl

To a solution of 250 mg (about 0.5 mmol) of ⌐Glu-His-Trp-NH—NH$_2$ in 3 ml of dimethylformamide 0.37 ml of 5.4N HCl/dioxane and 0.07 ml of tert.-butyl nitrite were added. The solution was stirred for 20 minutes at −10° C, cooled to −40° C, and 0.39 ml of N-ethylmorpholine and a solution of 453 mg of H-Ser-Tyr-Gly-Lys(Boc)-Arg-Pro-NH-$C_2H_5$ in 3 ml of dimethylformamide was added. The solution was allowed to react over night at 0° C, the solvent was distilled off in high vacuum and the residue was triturated with ether. In analogy to Example 1a) the crude substance was purified twice by column chromatography.

Yield of substance homogeneous with regard to thin layer chromatography: 106 mg $[\alpha]_D^{20} = -45.5°$ C (c=1, water).

According to UV — measuring and aminoacid analysis the product had a peptide content of about 80%.

Aminoacid analysis: Ser (0.62), Glu (1.00), Pro (1.02), Gly (1.00), Tyr (0.97), Lys(0.99), His (1.00), Arg (0.92).

EXAMPLE 4: (in analogy to the reaction scheme 2)

⌐Glu-His-Trp-Ser-Tyr-Gly-Orn(Boc)-Arg-Pro-NH-$C_2H_5$ a. H-Orn(Boc)-Arg-Pro-NH-$C_2H_5$ . 2 HCl

To a solution of 2.23 g (6 mmols) of H-Arg-Pro-NH-$C_2H_5$ . 2 HCl and 810 mg of HOBt in 10 ml of dimethylformamide 6.5 ml of N-ethylmorpholine and at 0° C, 11 g of DCC, dissolved in a small amount of dimethylformamide were added. The solution was stirred at 0° C and allowed to stand over night at room temperature. The deposit was suction-filtered and the filtrate was concentrated. The residue was distributed between water and ethyl acetate. The ethyl acetate phase was extracted with KHSO$_4$-solution, saturated NaHCO$_3$-solution and water, dried with Na$_2$SO$_4$ and concentrated. The ethyl acetate/petroleum ether was reprecipitated.

Yield: 26.8 g (88%), melting point: 123° – 125° C.

b. H-Ser-Tyr-Gly-Orn(Boc)-Arg-Pro-NH-$C_2H_5$ . 2 HCl

To a solution of 3.2 g (5.5 mols) of H-Orn(Boc)-Arg-Pro-NH-$C_2H_5$ . 2 HCl, 3.0 g (5.5 mols) of Z-Ser-Tyr(Bzl)-Gly-OH and 740 mg (5.5 mols) of HOBt in 10 ml of dimethylformamide 143 ml of N-ethylmorpholine and 1.2 g of DCC were added. The whole was stirred for 2 hours at 0° C and allowed to stand for three days at 4° C. The deposit was suction-filtered, the filtrate concentrated and the residue was triturated twice with saturated NaHCO$_3$-solution. The methylene chloride/ether was reprecipitated. 2.3 g of amorphous substance were obtained which were hydrogenated catalytically in methanol in analogy to Example 1(a).

Yield: 2.1 g.

The substance was purified by column chromatography in analogy to Example 1(a).

Yield: 830 mg of amorphous substance homogeneous by thin layer chromatography, $[\alpha]_D^{20} = -31.3°$ (c=1, methanol).

c. ⌐Glu-His-Trp-Ser-Tyr-Gly-Orn(Boc)-Arg-Pro-NH-$C_2H_5$-diacetate 250 mg(about 0.5 mmol) of Glu-His-Trp-NH-NH$_2$ were reacted in analogy to Example 3(e) with 496.5 mg of H-Ser-Tyr-Gly-Orn(Boc)-Arg-Pro-NH-$C_2H_5$ . 2 HCl. In analogous manner as in Example 1(a) the crude product was purified by column chromatography. The fractions containing the substance were concentrated and chromatographed in water over Dowex 1 × 2 (acetate form). The acetate thus prepared was purified again in analogy to Example 1(a) by column chromatography. Yield: 173 mg $[\alpha]_D^{22} = -49.5°$ (c=1, water). According to UV spectrum the substance had a peptide content of about 85%.

Amino acid analysis: Ser (0.67), Glu (1.02), Pro (1.01), Gly (1.00), Tyr (0.95), Orn (0.99), His (1.01), Arg (0.93).

EXAMPLE 5: (in analogy to the reaction scheme 2)

⌐Glu-His Trp-Ser-Tyr-Gly-Glu(OBu$^t$)-Arg-Pro-NH-$C_2H_5$-diacetate a. H-Glu(OBu$^t$)-Arg-Pro-NH-$C_2H_5$ . 2 HCl To a solution of 2.23 g (6 mmols) of H-Arg-Pro-NH-$C_2H_5$ . 2 HCl and 810 mg of HOBt in 10 ml of dimethylformamide 1.56 ml of N-ethylmorpholine and 3.1 g of Z-Glu(OBu$^t$)-OTcp were added. After five hours the solution was concentrated, the residue dissolved in ethyl acetate and extracted three times with saturated NaHCO$_3$-solution, dried with Na$_2$SO$_4$ and concentrated. The residue was hydrogenated catalytically in methanol in analogy to Example 1(a).

Yield: 2.7 g (78%) of an amorphous substance, not homogeneous with regard to thin layer chromatography (contaminated by about 5 by-products).

b. H-Ser-Tyr-Gly-Glu(OBu$^t$)-Arg Pro-NH-C$_2$H$_5$

To a solution of 2.7 g (4.7 mmols) of H-Glu(OBu$^t$)-Arg-Pro-NH-C$_2$H$_5$ . HCl, 2.5 g (4.7 mmols) of Z-Ser-Tyr(Bzl)-Gly-OH and 635 g of HOBt in 10 ml of dimethylformamide 1.22 ml of N-ethylmorpholine and at 0° C 1.06 g of DCC were added. The whole was stirred for one hour at 0° C and allowed to stand over night at room temperature. The deposit was suction-filtered and the filtrate concentrated. The residue was triturated twice with a NaHCO$_3$-solution, dissolved in ethyl acetate, dried with Na$_2$SO$_4$ and concentrated. Isopropanol/ether was precipitated. 3.4 g of an amorphous mass were obtained which were hydrogenated catalytically in methanol in analogy to Example 1(a). The crude product was purified by column chromatography in analogy to Example 1(a).

Yield of amorphous substance homogeneous with regard to thin layer chromatography: 1.8 g (44% calculated on H-Glu(OBu$^t$)-Arg-Pro-NH-C$_2$H$_5$ . 2 HCl), $[\alpha]_D^{20} = -21.3°$ (c=1, methanol).

c. ⌐Glu-His-Trp-Ser-Tyr-Gly-Glu(OBu$^t$)-Arg-Pro-NH-C$_2$H$_5$-diacetate 500 mg (about 1 mmol) of ⌐Glu-His-Trp-NH-NH$_2$ were reacted in analogy to Example 3(e) with 863.9 mg (1 mmol) of H-Ser-Tyr-Gly-Glu(OBu$^t$)-Arg-Pro-NH-C$_2$H$_5$ . 2 HCl. In analogy to Example 4(c) the crude product was purified.

Yield: 408 mg, $[\alpha]_D^{20} = -43.7°$ (c=1, water).

According to the UV spectrum the substance had a peptide content of 87%.

Amino acid analysis: Ser (0.65), Glu (2.05), Pro (0.99), Gly (1.00), Tyr (0.96), His (1.00), Arg (0.91).

EXAMPLE 6: (in analogy to the reaction scheme 2)

⌐Glu-His-Trp-Ser-Tyr-Gly-Ser(Bu$^t$)-Arg-Pro-NH-C$_2$H$_5$ a. H-Ser(Bu$^t$)-Arg-Pro-NH-C$_2$H$_5$ . 2 HCl

To a solution of 2.23 g (6 mmols) of H-Arg-Pro-NH-C$_2$H$_5$ .2 HCl and 810 mg of HOBt in 10 ml of dimethylformamide 1.56 ml of N-ethylmorpholine and 3.12 g of Z-Ser(Bu$^t$)-OTcp were added and the whole was stirred at room temperature. Then it was concentrated in vacuum, the residue was dissolved in ethyl acetate and the solution was extracted twice with saturated NaHCO$_3$-solution, dried over Na$_2$SO$_4$ and concentrated. The residue was triturated with ether and dried at the high vacuum. 2.3 g of amorphous substance were obtained, which in analogy to Example 1(a) were hydrogenated catalytically in methanol.

Yield: 2.7 g (81%) of amorphous substance. Not homogeneous with regard to thin layer chromatography (contaminated by about 5 by-products).

b. H-Ser-Tyr-Gly-Ser(Bu$^t$)-Arg-Pro-NH-C$_2$H$_5$ . 2 HCl

To a solution of 2.8 g (5.5 mmols) of H-Ser(Bu$^t$)-Arg-Pro-NH-C$_2$H$_5$ . 2 HCl, 3.0 g of Z-Ser-Tyr(Bzl)-Gly-OH (5.5 mmols) and 740 mg of HOBt in 10 ml of dimethylformamide 1.43 ml of N-ethylmorpholine and at 0° C 1.2 g of DCC were added. The whole was stirred for 2 hours at 0° C and allowed to stand at 4° C during the weekend. The deposit was suction-filtered, the filtrate concentrated and the residue was triturated twice with saturated NaHCO$_3$-solution. The substance was suction-filtered and dried. 2.6 g of amorphous substance were obtained which were hydrogenated catalytically in methanol in analogy to Example 1(a). In analogous manner as in Example 1(a) the crude substance was purified by column chromatography.

Yield: 885 mg (20% calculated on H-Ser(Bu$^t$)-Arg-Pro-NH-C$_2$H$_5$ . 2 HCl) of amorphous substance homogeneous with regard to thin layer chromatography. $[\alpha]_D^{20} = -31.2°$ (c=1, methanol).

c. ⌐Glu-His-Trp-Ser-Tyr-Gly-Ser(Bu$^t$)-Arg-Pro-NH-C$_2$H$_5$-diacetate 250 mg (about 0.5mmol) of ⌐Glu-His-Trp-NH-NH$_2$ were reacted in analogy to Example 3(e) with 410.9 mg (0.5mmol) of H-Ser-Tyr-Gly-Ser(Bu$^t$)-Arg-Pro-NH-C$_2$H$_5$ . 2 HCl. In analogous manner as in Example 4(c) the crude product was purified.

Yield: 191 mg, $[\alpha]_D^{20} = -53.2°$ (c=1, water).

According to the UV spectrum the substance had a peptide content of 78%.

Aminoacid analysis: Ser (1.4), Glu (1.02), Pro (0.98), Gly (1.00), Tyr (0.95), His (1.01), Arg (0.95).

EXAMPLE 7:

⌐Glu-His-Trp-Ser-Tyr-Gly-Cys(Bu$^t$)-Arg-Pro-NH-C$_2$H$_5$ a. Boc-Cys(Bu$^t$)-OH .DCHA 12.1 g of cysteine and 15 g of tert.-butanol were dissolved in 100ml of trifluoro-acetic acid. The solution was allowed to stand for 115 hours at room temperature and concentrated. The residue was triturated with ether and suction-filtered.

Yield: 22.5 g.

The substance obtained above was suspended in 150 ml of a dioxane-water mixture (8:2) and mixed with 27.3 g of Boc-azide. While stirring, 2N NaOH were added dropwise while stirring at room temperature under pH-stat-conditions (pH 9.5–10), until the sodium hydroxide solution was no longer consumed. The solution was neutralized, concentrated, the residue was taken up in water and extracted with ether. The aqueous solution was acidified to pH 3 with a KHSO$_4$-solution and extracted twice with ether. The combined ethyl acetate phases were extracted once with water and dried over Na$_2$SO$_4$. The ethyl acetate phase was concentrated. The residue was dissolved in petroleum ether and mixed with dicyclohexyl amine until a basic reaction. The mixture was cooled and the crystals were suction-filtered.

Yield: 29.5 g (64%), melting point: 185° – 187° $[\alpha]_D^{29} = +9.4°$ (c=1, methanol).

b. Boc-Cys(Bu$^t$)-OTcp 9.2 g (20 mmols) of Boc-Cys(Bu$^t$)—OH.DCHA were distributed at 0° between 50 ml of ether and 22 ml of 1N H$_2$SO$_4$. When everything was dissolved, the ether phase was separated, washed once with water, dried with Na$_2$SO$_4$ and concentrated.

Yield: 4.5 g of an oily substance.

4.16 g of the substance obtained above (15 mmols) of Boc-Cys(Bu$^t$)-OH) were dissolved together with 2.96 g (15 mmols) of 2.4.5-trichlorophenol in 30 ml of ethyl acetate. At 0° C 3.3 g of DCC were added, the whole was stirred for one hour at 0° C, and the solution was allowed to stand over night at room temperature. The deposit was suction-filtered, concentrated and crystallized from petroleum ether.

Yield: 6.7 g (98% calculated on Boc-Cys(Bu$^t$)-OH), melting point: 52° – 54°, $[\alpha]_D^{20} = -18.0°$ (c=1, in ethyl acetate)

c. H-Cys(Bu$^t$)-Arg-Pro-NH-C$_2$H$_5$ . 2 HCl

To a solution of 2.23 g (6 mmols) of H-Arg-Pro-NH-C$_2$H$_5$ HCl and 810 mg of HOBt in 10 ml of dimethylformamide 1.56 ml of N-ethylmorpholine and 2.8 g of Boc-Cys(Bu$^t$)-OTcp were added. After 10 minutes the solution was concentrated and the residue distributed between ethyl acetate and NaHCO$_3$-solution. The ethyl acetate phase was dried with Na$_2$SO$_4$ and concentrated.

Yield: 2.7 g of an amorphous substance.

The substance obtained above was dissolved in 11 ml of a 6N HCl/dioxane solution and stirred for two hours at room temperature. Subsequently it was concentrated and triturated with ether. 2.15 g (67%) of an amorphous substance remained which were further processed without any further purification.

d. H-Ser-Tyr-Gly-Cys(Bu$^t$)-Arg-Pro-NH-C$_2$H$_5$-diacetate

To a solution of 2.15 g (4 mmols) of H-Cys(Bu$^t$)-Arg-Pro-NH-C$_2$H$_5$ . 2 HCl, 540 mg of HOBt and 2.0 g of Z-Ser-Tyr(Bzl)-Gly-OH in 10 ml of dimethylformamide 1.04 ml of N-ethylmorpholine and at 0° C 880 mg of DCC were obtained. The mixture was allowed to stand for one hour at 0° C and over night at room temperature. The deposit was suction-filtered and the filtrate was concentrated. The residue was triturated twice with NaHCO$_3$-solution, dissolved in methylene chloride and dried over Na$_2$SO$_4$. The solution was concentrated, the residue triturated with ether. Yield: 3.6 g (91%).

The 3.6 g of substance obtained above (=3.63 mmols) of Z-Ser-Tyr(Bzl)-Gly-Cys(Bu$^t$)-Arg-Pro-NH-C$_2$H$_5$ were dissolved in methanol. 1.9 ml of N-ethylmorpholine (=4 equivalents) were added and hydrogenated catalytically on the Pd catalyst. In analogy to Example 1(a) the substance was purified by partition chromatography on Sephadex LH 20.

Yield: 1.01 g (30% calculated on Z-Ser-Tyr(Bzl)-Gly-OH) $[\alpha]_D^{21} = -31.1°$ (c=1, in methanol).

e. ⌐Glu-His-Trp-Ser-Tyr-Gly-Cys(Bu$^t$)-Arg-Pro-NH-C$_2$H$_5$-diacetate

To a solution of 250 mg of ⌐Glu-His-Trp-NH-NH$_2$ in 3 ml of dimethylformamide 0.33 ml of 6.04N HCl/dioxane were added at −30° C and 0.6 ml of a 10% tert.-butylnitrite/dioxane solution. Temperature was raised to −10° C and the whole was stirred for 20 minutes at this temperature. Then the solution was cooled to −40° C, 418.9 mg (0.5 mmol) of H-Ser-Tyr-Gly-Cys(Bu$^t$)-Arg-Pro-NH—C$_2$H$_5$ . 2 CH$_3$COOH and 0.39 ml of N-ethylmorpholine and the mixture was allowed to stand over night at 0° C. The next day it was concentrated and the residue was triturated with ether. The crude product was chromatographed in water over Dowex 1 × 2 (acetate form). The acetate thus prepared was purified on a carboxymethyl cellulose column (90 × 1.5 cm), equilibrated with 0.002 m of NH$_4$-acetate solution. The substance was added in a dissolved state in 0.002m NH$_4$-acetate solution. It was eluted with a 0.002 m NH$_4$ solution in which the gradient of a 0.1 m NH$_4$-acetate solution was established (mixed volume 250 ml). The fractions containing the desired peptide were freeze-dried twice.

Yield: 227 mg, $[\alpha]_D^{25} = -48.6°$ (c = 1, in water).

According to UV spectrum the substance had a content of peptide of 78.4% (= 30% yield).

EXAMPLE 8

⌐Glu-His-Trp-Ser-Tyr-D-Ala-Cys(Bu$^t$)-Arg-Pro-NH-C$_2$H$_5$ a. Z-Ser-Tyr(Bzl)-OH

To a suspension of 5.52 g (20 mmols) of H-Tyr(Bu$^t$)-OH in 60 ml of dimethylacetamide.7.68 g of Z-Ser-OOBt were added and the whole was stirred for six hours at room temperature. The undissolved material was suction-filtered and the filtrate cooled to 0° C was mixed with 300 ml of water. The deposit was suction-filtered, washed with a dimethylacetamide/water mixture (1:10) and water and stirred with 1N H$_2$SO$_4$. It was suction-filtered again and washed with water and dried. The ethyl acetate/petroleum ether was recrystallized.

Yield: 7.35 g (75%), melting point: 166° C, $[\alpha]_D^{20} = +20.9°$ (c=1, in methanol).

b. H-Ser-Tyr-D-Ala-Cys(Bu$^t$)-Arg-Pro-NH-C$_2$H$_5$-diacetate

To a solution of 3.6 g (6.8 mols) of H-Cys(Bu$^t$)-Arg-Pro-NH-C$_2$H$_5$ . 2 HCl and 920 mg of HOBt in 10 ml of dimethylformamide 1.77 ml of N-ethylmorpholine and 2.74 g of Z-D-Ala-OTcp were added. After 30 minutes it was concentrated and the residue was distributed between ethyl acetate and saturated NaHCO$_3$-solution. The ethyl acetate solution was dried over Na$_2$SO$_4$ and evaporated. The oily residue (5.5 g of Z-D-Ala-Cys(Bu$^t$)-Arg-Pro-NH-C$_2$H$_5$) was dissolved in methanol. After addition of 4.3 ml of N-ethylmorpholine and a Pd/BaSO$_4$-catalyst hydrogen was passed through the solution during 16 hours. Then the catalyst was suction-filtered, the filtrate was concentrated and the residue was triturated with ether.

Yield: 2.4 g of H-D-Ala-Cys(Bu$^t$)-Arg-Pro-NH-C$_2$H$_5$ (= 59%).

1.27 g (= 2.4 mmols) of H-D-Ala-Cys(Bu$^t$)-Arg-Pro-NH-C$_2$H$_5$ were dissolved together with 1.18 g of Z-Ser-Tyr(Bzl)-OH and 322 mg of HOBt in a small amount of dimethylformamide. 0.31 ml of N-ethylmorpholine and at 0° C 530 mg of DCC were added, the whole was stirred for one hour and allowed to stand over night at room temperature. The deposit was suction-filtered, the filtrate was concentrated and the residue triturated twice with a NaHCO$_3$-solution and once with water and suction-filtered.

Yield: 2.7 g of Z-Ser-Tyr(Bzl)-D-Ala-Cys(Bu$^t$)-Arg-Pro-NH-C$_2$H$_5$.

The substance obtained above was dissolved in a mixture of dimethylformamide and methanol (as 1:1). 1.4 ml of N-ethylmorpholine, Pd/BaSO$_4$-catalyst were added and for 24 hours hydrogen was passed through the solution. The catalyst was suction-filtered and the residue was purified by partition chromatography on Sephadex LH 20 in analogy to Example 1(a).

Yield: 1.24 g of H-Ser-Tyr-D-Ala-Cys(Bu$^t$)-Arg-Pro-NH-C$_2$H$_5$-diacetate (= 58% calculated on Z-Ser-Tyr(Bzl)—OH). $[\alpha]_D^{20} = -28.9°$ (c=1, in methanol).

c. ⌐Glu-His-Trp-Ser-Tyr-D-Ala-Cys(Bu$^t$)-Arg-Pro-NH-C$_2$H$_5$-diacetate

In analogy to Example 7(e) 448.5 mg (0.5 mol) of H-Ser-Tyr-D-Ala-Cys(Bu$^t$)-Arg-Pro-NH-C$_2$H$_5$-diacetate were reacted with ⌐Glu-His-Trp-NH-NH$_2$, worked up and purified over Dowex 1 × 2 (acetate form) and carboxymethyl cellulose. Since the substance was not completely pure, it was purified in analogy to Example 1(a) on Sephadex LH 20.

Yield: 120 mg. $[\alpha]_D^{20} = -38.6°$ (c=1, in water).

According to UV spectrum the content of peptide base was 80%.

EXAMPLE 9:

⌐Glu-His-Trp-Ser-Tyr-D-Leu-Cys(Bu$^t$)-Arg-Pro-NH-C$_2$H$_5$ a. H-Ser-Tyr-D-Leu-Cys(Bu$^t$)-Arg-Pro-NH-C$_2$H$_5$-diacetate In analogy to Example 8(b) 3.6 g (6.8 mmols) of H-Cys(Bu$^t$)-Arg-Pro-NH-C$_2$H$_5$ . 2 HCl were reacted with 3 g of Z-D-Leu-OTcp and worked up. The oily residue (6.1 g of contaminated Z-D-Leu-Cys(Bu$^t$)-Arg-Pro-NH—C$_2$H$_5$) was hydrogenated catalytically in analogy to Example 8(b). Yield: 2.5 g (57%). The compound was strongly contaminated and purified over Sephadex LH 20 in analogy to Example 1(a). Yield: 1.734 g (40%) of H-D-Leu-Cys(Bu$^t$)-Arg-Pro-NH-C$_2$H$_5$-diacetate. The 1.734 g (2.7 mmols) of H-D-Leu-Cys(Bu$^t$)-Arg-Pro-NH-C$_2$H$_5$-acetate were reacted in analogy to Example 8(b) with 1.33 g of Z-Ser-Tyr(Bzl)-OH, 0.71 ml of N-ethyl morpholine, 3.65 mg of HOBt and 595 mg of DCC in 5 ml of dimethylformamide and worked up. The substance obtained (2.45 g of Z-Ser-Tyr(Bzl)-D-Leu-Cys(Bu$^t$)-Arg-Pro-NH-C$_2$H$_5$) was hydrogenated catalytically in analogy to Example 8(b) and purified over Sephadex LH 20.

Yield: 1.43 g of H-Ser-Tyr-D-Leu-Cys(Bu$^t$)-Arg-Pro-NH-C$_2$H$_5$-diacetate (= 56% calculated on Z-Ser-Tyr(Bzl)-OH). $[\alpha]_D^{20} = -13.1°$ (c=1, in methanol).

b. ⌐Glu-His-Trp-Ser-Tyr-D-Leu-Cys(Bu$^t$)-Arg-Pro-NH-C$_2$H$_5$-diacetate

In analogy to Example 7(e) 469.5 mg (0.5 mol) of H-Ser-Tyr-D-Leu-Cys(Bu$^t$)-Arg-Pro-NH-C$_2$H$_5$-diacetate were reacted with Glu-His-Trp-NH-NH$_2$, worked up and purified over Dowex 1 × 2 (acetate form) and carboxymethyl cellulose. Since the substance was not yet completely pure it was purified in analogy to Example 1(a) on Sephadex LH 20.

Yield: 112.1 mg. $[\alpha]_D^{20} = -28.5°$ (c=1, in water).

According to UV spectrum the content of the peptide base was 82%.

EXAMPLE 10:

⌐Glu-His-Trp-Ser-Tyr-D-Leu-Ser(Bu$^t$)-Arg-Pro-cyclopropyl amide a. Z-Pro-cyclopropyl amide To a solution of 124.6 g (0.5 mol) of Z-Pro-OH, 34.8 ml of cyclopropyl amine and 67.5 g HOBt in 200 ml of absolute tetrahydrofurane 110 g of DCC were added at 0° C, the solution was stirred for one hour at 0° C and allowed to stand over night at room temperature. The deposit was suction-filtered and the filtrate was concentrated. The residue was taken up in ethyl acetate and extracted with saturated NaHCO$_3$-solution, 2N HCl, saturated NaHCO$_3$-solution and water, dried over Na$_2$SO$_4$ and concentrated. The residue was triturated with petroleum ether and suction-filtered. The ethyl acetate/petroleum ether was recrystallized.

Yield: 90.8 g (63%), melting point: 124° – 126°, $[\alpha]_D^{24} = -45.5°$ (c=1, in methanol).

b. H-Pro-cyclopropylamide . HCl 90.8 g (0.315 mol) of Z-Pro-cyclopropyl amide were dissolved in 500 ml of methanol. A Pd/BaSO$_4$-catalyst was added and the whole was hydrogenated by passing, while stirring, hydrogen through the solution. The pH-value of the solution was maintained at 4.5 with the aid of an autotitrator by addition of methanolic hydrochloric acid. When hydrogenation was finished the catalyst was suction-filtered and the filtrate concentrated. The residue was triturated with ether.

Yield: 60 g (100%), melting point: 168° – 170° C.

c. Z$_3$-Arg-Pro-cyclopropyl amide

To a solution of 28.84 g (50 mmols) of Z$_3$-Arg-OH, 9.5 g (50 mmols) of H-Pro-cyclopropyl amide . HCl and 6.75 g (50 mmols) of HOBt in 100 ml of methylene chloride and 25 ml of dimethylformamide 6.5 ml of N-ethylmorpholine were added and at 0° C a solution of 11 g of DCC in a small amount of methylene chloride. The whole was allowed to stand for one hour at 0° C and over night at room temperature. The deposit was suction-filtered and the filtrate was concentrated. The residue was taken up in ethyl acetate and successively with water, saturated NaHCO$_3$-solution, 1N HCl and saturated NaHCO$_3$-solution, dried over Na$_2$SO$_4$ and concentrated. The ethyl acetate/petroleum ether was crystallized. The substance was still contaminated and was chromatographed on 250 g of silica gel in CH$_2$Cl$_2$/acetone mixtures (such as 9:1 and 8:2).

Yield: 22.8 g (64%), melting point: 171°, $[\alpha]_D^{21} = -33.0°$ (c=1, in methanol).

d. H-Arg-Pro-cyclopropylamide . 2 HCl 22 g (30.9 mmols) of Z$_3$-Arg-Pro-cyclopropylamide were hydrogenated catalytically in analogous manner as in Example (b). The residue was dried in high vacuum. An amorphous foam is obtained.

Yield: 11 g (89%).

e. H-Ser(Bu$^t$)-Arg-Pro-cyclopropylamide . 2 HCl

To a solution of 7.66 g (20 mmols) of H-Arg-Pro-NH-C$_2$H$_5$ . 2 HCl and 2.7 g of HOBt in 20 ml of dimethylformamide 5.2 ml of N-ethylmorpholine and at 0° C 9.6 g of Z-Ser(Bu$^t$)-OTcp were added. After two hours the solution was concentrated. The residue was dissolved in ethyl acetate and extracted three times with a NaHCO$_3$-solution, dried over Na$_2$SO$_4$ and concentrated. The residue was triturated with ether. The ether was decanted and the residue was dried at the high vacuum. 13.3 g of an amorphous substance remained which were hydrogenated catalytically in analogous manner as in Example (b).

Yield: 9.26 g of amorphous H-Ser(Bu$^t$)-Arg-Pro-cyclopropylamide . 2 HCl (= 88% calculated on H-Arg-Pro-NH-C$_2$H$_5$ . 2 HCl).

f. H-Ser-Tyr-D-Leu-Ser(Bu$^t$)-Arg-Pro-cyclopropylamide . 2 HCl

To a solution of 2.63 g (5 mmols) of H-Ser(Bu$^t$)-Arg-Pro-cyclopropylamide . 2 HCl and 675 mg of HOBt in 5 ml of dimethylformamide 1.3 ml of N-ethylmorpholine and 2.22 g of Z-D-Leu-OTcp were added. The solution was allowed to stand over night at room temperature and it was concentrated. The residue was taken up in ethyl acetate and extracted twice with saturated NaHCO$_3$-solution. The solution was dried over Na$_2$SO$_4$ and concentrated. The resulting oil (3.9 g) was hydrogenated catalytically in analogy to Example (b). 2.45 g of amorphous H-D-Leu-Ser(Bu$^t$)-Arg-Pro-cyclopropylamide . 2 HCl (= 76% calculated on Z-D-Leu-OTcp). The 2.45 g (3.82 mmols) of H-D-Leu-Ser(Bu$^t$)-Arg-Pro-cyclopropylamide . 2 HCl were dissolved together with 1.87 g of Z-Ser-Tyr(Bzl)-OH and 515 mg of HOBt in 10 ml of dimethylformamide. 0.99 ml of N-ethylmorpholine and at 0° C, 835 mg of DCC were added, the mixture was stirred for one hour at 0° C and allowed to stand over night at room temperature. The deposit was suction-filtered and the filtrate was concentrated. The residue was triturated twice with saturated NaHCO$_3$-solution and dissolved in CH$_2$Cl$_2$. The solution was dried over Na$_2$SO$_4$ and concentrated. The oily residue was hydrogenated catalytically in analogy to Example (b). The product was purified by partition chromatography on Sephadex LH 20 in analogy to the main patent.

Yield: 1.285 g of amorphous substance (34% calculated on Z-Ser-Tyr(Bzl)-OH), $[\alpha]_D^{20} = -20.1°$ (c=1, in methanol).

g. Glu-His-Trp-Ser-Tyr-D-Leu-Ser(Bu$^t$)-Arg-Pro-cyclopropylamide diacetate

To a solution of 250 mg of Glu-His-Trp-NH-NH$_2$ in 3 ml of dimethylformamide 0.33 ml of HCl/dioxane (6.04N) and 0.6 ml of a 10% tert.-butyl nitrite/dioxane solution were added; the solution was stirred for 20 minutes at −10° C and then, at −40° C, 445 mg (0.5 mmol) of H-Ser-Tyr-D-Leu-Ser(Bu$^t$)-Arg-Pro-cyclopropylamide . 2 HCl and 0.39 of N-ethylmorpholine were added. The mixture was allowed to stand over night, the next day the solvent was distilled off and the residue was triturated with ether. The substance was dissolved in water and chromatographed over Dowex 1 × 2 (acetate form). The acetate thus obtained was purified by gradient elution on carboxymethyl cellulose and by partition chromatography on Sephadex LH 20 (in analogy to main patent Example 1(a).

Yield: 123 mg = $-37.4°$ (c=1, in water).

According to UV spectrum the content of peptide base was 88%.

EXAMPLE 11

⌐Glu-His Trp-Ser-Tyr-D-Leu-Ser(Bu$^t$)-Arg-Pro-NH-C$_2$H$_5$ a. 2 HCl . H-Ser-Tyr-D-Leu-Ser(Bu$^t$)-Arg-Pro-NH-C$_2$H$_5$

To a solution of 2.57 g (5 mmols) of 2 HCl . H-Ser(-Bu$^t$)-Arg-Pro-NH-C$_2$H$_5$ and 675 mg of HOBt in 5 ml of dimethylformamide 1.3 ml of N-ethylmorpholine and 2.22 g of Z-D-Leu-OTcp were added at 0° C. After two hours the solution was concentrated and the residue was distributed between ethyl acetate and saturated NaHCO$_3$-solution. The ethyl acetate phase was dried over Na$_2$SO$_4$ and concentrated. The residue was triturated with ether. 2.8 g of substance were obtained which were dissolved in methanol (addition of 1N methanolic HCl at pH 4.5) and hyrogenated catalytically (Pd catalyst) at the autotitrator. When hydrogenation was finished the catalyst was suction-filtered, the filtrate concentrated and the residue was triturated with ether. 2.2 g of 2 HCl . D-Leu-Ser(Bu$^t$)-Arg-Pro-NH-C$_2$H$_5$ were obtained which were dissolved with 1.72 g of Z-Ser-Tyr(Bzl)—OH and 472 mg of HOBt in 7 ml of dimethylformamide. 0.91 ml of N-ethylmorpholine and at 0° C 770 mg of DCC were added to the solution, the whole was stirred for one hour at 0° C and allowed to stand over night at room temperature. The deposit was suction-filtered and the filtrate concentrated. The residue was triturated twice with saturated NaHCO$_3$-solution, dissolved in methylene chloride, dried over Na$_2$SO$_4$ and concentrated. The residue (3.35 g) was hydrogenated catalytically (Pd-catalyst) at the autotitrator (addition of 1N methanolic HCl at pH 4.5). When hydrogenation was finished the catalyst was suction-filtered, the filtrate was concentrated and purified by chromatography in analogy to Example 1(a) on Sephadex LH 20.

Yield: 1.45 g (=33% calculated on 2 HCl . H-Ser(-Bu$^t$)-Arg-Pro-NH-C$_2$H$_5$), $[\alpha]_D^{20} = -23.6°$, (c=1, in methanol).

b. ⌐Glu-His-Trp-Ser-Tyr-D-Leu-Ser(Bu$^t$)-Arg-Pro-NH-C$_2$H$_5$-diacetate 250 mg of ⌐Glu-His-Trp-NH-NH$_2$ were reacted in analogy to Example 3(e) with 439 mg (0.5mmol) of 2 HCl . H-Ser-Tyr-D-Leu-Ser(Bu$^t$)-Arg-Pro-NH-C$_2$H$_5$. The substance thus obtained was dissolved in water and chromatographed over Dowex 1 × 2 (acetate form). The acetate thus obtained was purified by gradient elution on carboxymethyl cellulose.

Yield: 280 mg, $[\alpha]_D^{20} = -28.3°$ (c=1, in water).

According to UV spectrum the content of peptide base was 66%.

EXAMPLE 12

⌐Glu-His-Trp-Ser-Tyr-Gly-Asp(OBu$^t$)-Arg-Pro-NH-C$_2$H$_5$ a. HCl . H-Asp(OBu$^t$)-Arg-Pro-NH-C$_2$H$_5$

To a solution of 2.23 g (6 mmols) of 2 HCl . H-Arg-Pro-NH-C$_2$H$_5$ in 10 ml of dimethylformamide 1.56 ml of N-ethylmorpholine and 2.5 g of Z-Asp(OBu$^t$)-ONSu were added at 0° C. The mixture was allowed to stand at room temperature and concentrated. The residue was dissolved in methanol and hydrogenated catalytically (Pd-catalyst) at the autotitrator (addition of 1N methanolic HCl at pH 4.5). When hydrogenation was finished the catalyst was suction-filtered, the filtrate was concentrated and the resulting residue was triturated twice with ether and dried at the high vacuum. 3.4 g of an amorphous foam remained.

b. 2 HCl . H-Ser-Tyr-Gly-Asp(OBu$^t$)-Arg-Pro-NH-C$_2$H$_5$

To a solution of 3.4 g of 2 HCl . H-Asp(OBu$^t$)-Arg-Pro-NH-C$_2$H$_5$ (6.2 mmols),o 3.4 g of Z-Ser-Tyr(Bzl)-Gly-OH (6.2 mmols) and 840 mg of HOBt in 15 ml of dimethylformamide 1.6 ml of N-ethylmorpholine and 1.36 g of DCC were added at 0° C. The whole was stirred for one hour at 0° C and for one day at room temperature. The deposit was suction-filtered and the filtrate concentrated. The residue was triturated twice with a 2N Na$_2$CO$_3$-solution and triturated once with water. The substance was centrifuged and dried. Then the substance was dissolved in methanol and hyrogenated catalytically (Pd catalyst) at the autotritator (addition of a 1N methanolic HCl at pH 4.5). When hydrogenation was finished the catalyst was suction-filtered and the filtrate concentrated. The residue was triturated with ether, suction-filtered and then purified chromatographically on Sephadex LH 20 in analogy to Example 1(a).

Yield: 2.184 g (= 36.4% calculated on 2 HCl . H-Arg-Pro-NH-C$_2$H$_5$). $[\alpha]_D^{20} = -31.4°$ (c=1, in methanol).

c. ⌐Glu-His-Trp-Ser-Tyr-Gly-Asp(/Bu$^t$)-Arg-Pro-NH-C$_2$H$_5$-diacetate 250 mg of Glu-His-Trp-NH-NH$_2$ were reacted in analogy to Example 3(e) with 425 mg (0.5 mol) of 2 HCl . H-Ser-Tyr-Gly-Asp(OBu$^t$)-Arg-Pro-NH-C$_2$H$_5$. The substance thus obtained was dissolved in water and chromatographed over Dowex 1 × 2 (acetate form). The acetate thus obtained was purified by gradient elution on carboxymethyl cellulose.

Yield: 230 mg, $[\alpha]_D^{20} = -43.6°$ (c=1, in water).

According to UV spectrum the content of peptide base was 74%.

We claim:
1. A peptide of the general formula

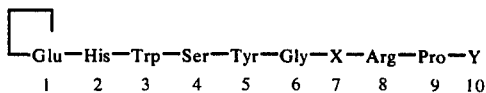

wherein X represents Ser(Bu$^t$), Cys(Bu$^t$), Asp(OBu$^t$), Glu (OBu$^t$), Orn(Boc) or Lys(Boc) and Y is glycinamide or a NH-alkyl group wherein the alkyl radical contains 1 to 3 carbon atoms and may be substituted by OH groups or halogen atoms, or Y is the NH-cyclopropyl radical and wherein Trp may be substituted by pentamethylphenyl alanine, Ser by Ala or Thr, Tyr by Phe, Gly by D-amino acids corresponding to the naturally occuring L-amino acids, Arg by Orn, Lys or homoarginine.

2. ⌐Glu-His-Trp-Ser-Tyr-Gly-Ser(Bu$^t$)-Arg-Pro-NHC$_2$H$_5$.
3. ⌐Glu-His-Trp-Ser-Tyr-Gly-Cys(Bu$^t$)-Arg-Pro-NHC$_2$H$_5$.
4. ⌐Glu-His-Trp-Ser-Tyr-Gly-Glu(OBu$^t$)-Arg-Pro-NHC$_2$H$_5$.
5. ⌐Glu-His-Trp-Ser-Tyr-D-Ala-Ser(Bu$^t$)-Arg-Pro-NHC$_2$H$_5$.
6. ⌐Glu-His-Trp-Ser-Tyr-D-Leu-Ser(Bu$^t$)-Arg-Pro-cyclopropylamide.
7. ⌐Glu-His-Trp-Ser-Tyr-D-Leu-Cys(Bu$^t$)-Arg-Pro-NH-C$_2$H$_5$.

* * * * *